US008367014B2

(12) United States Patent
Banerji

(10) Patent No.: US 8,367,014 B2
(45) Date of Patent: Feb. 5, 2013

(54) LOW-MASS SAMPLE BLOCK WITH RAPID RESPONSE TO TEMPERATURE CHANGE

(75) Inventor: Sunand Banerji, Stoneham, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 34 days.

(21) Appl. No.: 12/557,674

(22) Filed: Sep. 11, 2009

(65) Prior Publication Data

US 2010/0003725 A1 Jan. 7, 2010

Related U.S. Application Data

(60) Division of application No. 11/768,380, filed on Jun. 26, 2007, now Pat. No. 7,632,464, which is a continuation-in-part of application No. 11/479,426, filed on Jun. 29, 2006, now abandoned.

(51) Int. Cl.
*C12Q 1/68* (2006.01)

(52) U.S. Cl. ........ 422/407; 422/526; 422/553; 422/400; 206/509; 206/507; 435/6; 435/288.3

(58) Field of Classification Search ........................ None
See application file for complete search history.

(56) References Cited

U.S. PATENT DOCUMENTS

| | | | | | |
|---|---|---|---|---|---|
| 4,944,398 | A | * | 7/1990 | Gatt | 206/507 |
| 6,063,579 | A | * | 5/2000 | Bevirt et al. | 435/6 |
| 6,083,761 | A | * | 7/2000 | Kedar et al. | 506/30 |
| 6,555,792 | B1 | * | 4/2003 | Elsener et al. | 219/428 |
| 7,407,630 | B2 | * | 8/2008 | Reed et al. | 422/102 |

* cited by examiner

*Primary Examiner* — Sally Merkling
(74) *Attorney, Agent, or Firm* — Kilpatrick Townsend & Stockton LLP.; M. Henry Hienes

(57) ABSTRACT

A sample block for use in the polymerase chain reaction, DNA sequencing, and other procedures that involve the performance of simultaneous reactions in multiple samples with temperature control by heating or cooling elements contacting the bottom surface of the block is improved by the inclusion of hollows in the block that are positioned to decrease the mass of the block in the immediate vicinity of the wells.

2 Claims, 5 Drawing Sheets

LOW-MASS SAMPLE BLOCK WITH RAPID RESPONSE TO TEMPERATURE CHANGE

CROSS REFERENCES TO RELATED APPLICATIONS

This application is a division of, application Ser. No. 11/768,380, filed Jun. 26, 2007, now U.S. Pat. No. 7,632,464, which is a continuation-in-part of then application Ser. No. 11/479,426, filed Jun. 29, 2006. The contents of all applications cited in this paragraph are incorporated herein in their entirety.

BACKGROUND OF THE INVENTION

1. Field of the Invention

This invention resides in the field of laboratory apparatus for performing procedures that require simultaneous temperature control in a multitude of small samples arranged in a geometric array. This invention is of particular interest in systems utilizing unitary contoured multiple sample supports, commonly known as "sample blocks," in conjunction with thermoelectric modules for modulation and control of the temperature of the entire block or a section of the block.

2. Description of the Prior Art

The polymerase chain reaction (PCR) is one of many examples of chemical processes that require precise temperature control with rapid temperature changes between different stages of the procedure. PCR amplifies DNA, i.e., it produces multiple copies of a DNA sequence from a single copy. PCR is typically performed on a multitude of samples simultaneously in parallel manner, using instruments that provide reagent transfer, temperature control, and optical detection in a multitude of reaction vessels such as wells, tubes, or capillaries. Each sample in the process undergoes a sequence of process stages that are temperature-sensitive, with different stages performed at different temperatures and maintained for designated periods of time, and the sequence is repeated in cycles. Typically, a sample is first heated to about 95° C. to "melt" (separate) double strands, then cooled to about 55° C. to anneal (hybridize) primers to the separated strands, and then reheated to about 72° C. in a reaction mixture that contains nucleotide bases and DNA polymerase to achieve primer extension. This sequence is repeated to achieve multiples of the product DNA, and the time consumed by each cycle can vary from a fraction of a minute to two minutes, depending on the equipment, the scale of the reaction, and the degree of automation.

Nucleic acid sequencing is another example of a chemical process that involves temperature changes and a high degree of control, different temperatures being required for such steps as the denaturing and renaturing of the nucleic acid as well as enzyme-based reactions.

The successful performance of PCR, nucleic acid sequencing, and any other processes that involve a succession of stages at different temperatures requires accurate temperature control and fast temperature changes. As noted above, many of these processes involve the simultaneous processing of large numbers of samples, each having a relatively small volume, often on the microliter scale. In some cases, the procedure requires that certain samples be maintained at one temperature while others are maintained at another temperature, thus requiring the maintenance of different regions of the block at different temperatures and in some cases a temperature gradient. In both PCR and nucleic acid sequencing, the automated laboratory equipment that controls the temperature is known as a thermal cycler, and as noted above, many automated systems utilize a sample block with a multitude of wells arranged in the block in a geometrical array. The wells are either used as individual reaction vessels for each of the samples by placing the samples directly in the wells, or as a support for a disposable plastic plate which itself contains an array of wells conforming in shape to the wells of the block. When a disposable plate is used, the plate is placed directly over the block with the contours of the plate and the block in full contact. The wells in the plate then serve as the reaction vessels while the underlying block provides rigid support to the plate and close temperature control due to the intimate surface contact.

The temperature of the sample block in many of these systems, and hence the temperatures of individual samples, are usually modified by the use of thermoelectric modules, although electrical heating, air cooling, liquid cooling, and refrigeration can also be used. Thermoelectric modules are semiconductor-based electronic components that function as small heat pumps through use of the Peltier effect, causing heat to flow in a direction determined by the direction in which electric current is passed through the component. Thermoelectric modules are particularly useful due to their ability to provide localized temperature control with fast response, and to the fact that they are driven electronically which provides a high degree of control. The modules are typically arranged edge-to-edge with their heat transfer surfaces in full contact with the flat undersurface of the sample block.

Thermoelectric modules and any components that serve as heat exchange units function most effectively when pressed tightly against the sample block. For optimal thermal response, a sample block must be stiff and made of a material that has a high heat transfer coefficient and a low thermal mass. Stiffness also benefits the reactions themselves by keeping the wells in planar alignment and preventing the block from bowing or otherwise becoming distorted in response to the applied mechanical pressure. The rate at which the samples in the wells are heated or cooled will vary with the mass of the block. The lower the mass of the block, the faster the temperature changes are transmitted to the samples. Thus, while metals such as aluminum offer the requisite stiffness, particularly near the bottom surface of the block, their mass retards the heat transfer to the samples. This is true whether the samples reside in the wells of the block or in a disposable plate in contact with the block. These and other concerns are addressed by the present invention.

SUMMARY OF THE INVENTION

The present invention resides in a sample block that has a reduced mass to maximize the speed at which the block is heated or cooled by the heat transfer components. In this specification and the appended claims, the sample block is also referred to as a "multiple sample support," which term is intended to encompass blocks whose wells are used directly as the reaction vessels for the individual samples, as well as blocks that are used as a support base for a disposable reaction plate that has wells that fit inside the wells of the block. In the latter case, the wells of the disposable, overlying plate serve as the reaction vessels while the block provides the plate with rigidity and temperature control.

The reduction in mass of the sample block is achieved by a series of hollows in the block, arranged around the sample wells in positions that retain the sample wells intact, but positioned to decrease the mass of the block in the immediate vicinity of the sample wells. In certain embodiments, the hollows form parallel non-intersecting channels that run parallel to the top and bottom surfaces of the sample block, while in other embodiments, the hollows form a network of intersecting passages, all parallel to the top and bottom surfaces of the block, to provide a greater open volume in the block. In still further embodiments, the hollows are inverted wells positioned between the sample wells, the inverted wells being open at the bottom surface of the sample block and having centerlines that are perpendicular to the top and bottom surfaces of the sample block, i.e., parallel to the centerlines of the sample wells. In all of these embodiments and in the invention as a whole, the passages are preferably arranged so that they do not intersect the sample wells. The block will thus provide maximal surface contact with a disposable sample plate, or when the block itself receives the samples directly, the wells of the block that are open to the top will be able to retain the samples. In preferred embodiments in which the hollows are extended channels that run parallel to the top and bottom surfaces of the block, the block is rigid and the channels are preferably located on or close to the neutral plane of the block, i.e., the plane in which the block is subjected to neither a compression force nor an expansion force when a bending stress is imposed on the block from either above or below. This provides the block in these embodiments with maximum stiffness when subjected to such a bending stress. The effect is similar to that achieved by an I-beam in construction engineering. In embodiments in which the hollows are inverted wells open at the bottom surface of the block, an advantage that these have over the channels that run parallel to the top and bottom surfaces is a greater speed to a wider range of block sizes. These embodiments are ideally suited, for example, to a 384-well (16×24) block with a 4.5-mm center-to-center well spacing.

To minimize confusion, the term "sample wells" is used herein to denote the wells that are open at the top surface of the sample block and are intended either to serve as receptacles for the samples themselves or as indentations to receive the lower surfaces of the wells of a disposable sample plate when such a plate is used. The term "sample wells" is also used to distinguish over the "inverted wells" in those embodiments that include such wells, and also to distinguish over other wells that are open at the top surface of the sample block and are included for purposes other than retaining samples or receiving the wells of a disposable plate. The inverted wells and any other wells that serve to reduce the mass of the sample block will also be referred to as "inverted mass reduction wells."

An additional and independently novel feature of certain multiple sample supports (i.e., sample blocks) of this invention arises when the multiple sample support is used in combination with a disposable sample plate that is contoured to form wells complementary in shape to the wells of the sample block for extended surface contact and high thermal response. When the block also contains indentations in its upper surface for purposes of mass reduction, in addition to the wells that are designed to receive the wells of the sample plate, there is a risk that the user will misalign the plate relative to the block and position the plate such that the wells of the plate are inserted into the (top-opening) mass reduction indentations rather than the wells of the block that are intended for receiving the sample plate wells. In certain aspects of the present invention, this risk of misalignment is avoided by arranging the mass reduction indentations in the block in an array that is not fully complementary with the array of sample wells in the disposable sample plate. Thus, while both sets of wells may be in rectangular arrays with the same center-to-center spacing, one or more of the top-opening mass reduction indentations in the block may be omitted, leaving in its place either a platform or a contour that does not accept a well of the disposable plate. In this way, at least one of the wells of the disposable sample plate will abut the platform or non-receiving contour on the top surface of the block if the disposable plate is oriented with its wells above the mass reduction indentations rather than the complementary wells.

The invention also resides in a method for amplifying a plurality of samples of DNA in wells of a multi-well sample plate by PCR, the method involving thermally cycling the samples in the wells of the sample plate to separate double strands of the DNA into single strands, anneal oligonucleotide primers to target sequences of the single strands, and extend the primers in the presence of DNA polymerase, all steps being performed under conventional PCR conditions while the sample plate is supported by the multiple sample support in an of its embodiments described above.

These and other features, embodiments, objects, and advantages of the invention will be apparent from the descriptions that follow.

DETAILED DESCRIPTION OF THE INVENTION AND PREFERRED EMBODIMENTS

Figure 1:
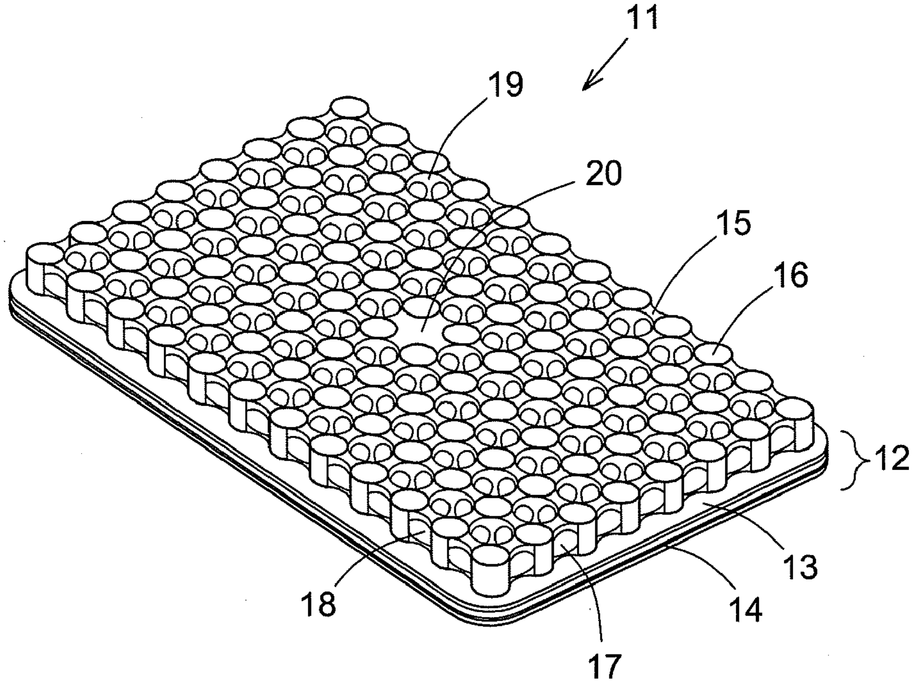
FIG. 1 is a perspective view from above of a sample block in accordance with the present invention.

The sample block, or multiple sample support, of the present invention is preferably of unitary construction, which means that the block is preferably formed as a single piece, such as by machining or molding, rather than by joining together individually formed portions by mechanical or chemical means. The block is also rigid and preferably made of a material that possesses both high stiffness and high thermal conductivity. Examples of suitable metals are aluminum, copper, iron, magnesium, silver, and alloys of these metals. Non-metallic materials such as aluminum oxide, aluminum nitride, and carbon, and particularly composites of these materials, can also be used. Aluminum metal is currently preferred. The sample wells in sample blocks of the prior art are most commonly arranged in a rectangular array, i.e., in evenly spaced rows and columns, and preferred sample blocks of the present invention will likewise have wells in a planar, preferably rectangular, array. The number of sample wells can vary widely and is not critical to this invention. Sample blocks with as few as four sample wells can benefit from this invention, as can sample blocks with sample wells numbering in the thousands. A preferred range of the number of sample wells is 4 to 4,000, a more preferred range is 12 to 400, with 16 to 400 even more preferred, and the most common implementations are expected to be blocks with 96 sample wells in a 12×8 array and blocks with 48 sample wells in a 6×8 array. The spacing between the sample wells can likewise vary, but in most cases, the center-to-center spacing will likely be within the range of 4 mm (0.15 inch) to 12 mm (0.45 inch).

In embodiments in which the hollows are elongated and extend parallel to the top and bottom surfaces of the sample block, the hollows can either be closed cavities or open passages. Open passages are preferred for ease of manufacture and the greater mass reduction that they offer. The passages can be open at the edges of the sample block and extend the full length or width of the block. They can be straight passages extending lengthwise along the block between each adjacent pair of rows of sample wells, or widthwise between each adjacent pair of columns sample wells. For greater mass reduction, passages extending in both directions can be included, intersecting at each juncture, to form a network of open volume within the block. For still further mass reduction, openings in the top surface of the block can be included that lead to the passages or the network.

In one presently contemplated embodiment, the thickness of the block as a whole is about 9.5 mm (0.375 inch), the hollows are elongated passages that are parallel to the top and bottom surfaces and of circular cross section with diameters of 4.5 mm (0.18 inch), and the centers of the passages are 6 mm (0.24 inch) from the bottom surface of the block.

In embodiments in which the hollows are inverted mass reduction wells that are open at the bottom surface of the sample block with centerlines parallel to those of the sample wells, both the sample wells and the hollows can cross the midplane of the sample block, particularly if the hollows are positioned at the intersections of diagonal lines connecting the centers of the sample wells. In these embodiments as well, both the sample wells and the inverted, mass reduction wells are or circular cross section, and the sample wells are preferably tapered so that they are wider at the mouth than at the base of each well. The inverted, mass reduction wells can also be tapered in the opposite direction, wider at their mouths than at their inverted bases, the mouths of the sample wells being at the top surface of the block while the mouths of the mass reduction wells being at the bottom surface. The tapers in both sets of wells can either be smooth tapers or staged tapers. Staged tapers can consist of a succession of two or more non-tapering segments of successively decreasing diameter, or combinations of tapering segments and non-tapering segments. Also in these embodiments, it is preferred that there be no other wells or other openings at the top surface of the sample block.

In view of the range of possibilities set forth above, the present invention is susceptible to variation in terms of the configurations and arrangements of the wells and the hollows. The hollows for example can be any cross-sectional shape or any combination of shapes. A detailed review of one particular embodiment however will provide an understanding of the function and operation of the invention in each of its embodiments. The figures hereto depict two such embodiments.

FIG. 1 is a perspective view of a sample block 11 with a 12×8 array of wells in a standard spacing. The block is a single piece of machined metal with a relatively thick base 12 that is slightly longer and wider than the remainder of the block to form a flange 13. Encircling the edge of the base is a groove 14 to accommodate an O-ring. The center section of the block that is bordered by the flange rises to the top surface 15 of the block. The top surface 15 is flat and planar and is interrupted by the openings of the sample wells 16. The hollows (which are more clearly shown in FIGS. 3 through 7) are a network of passages below the top surface 15. The centerlines or longitudinal axes (not shown) of these passages are parallel to the top surface 15, and the open ends 17, 18 of the passages are visible along the edges of the raised center section (only two such edges being visible in FIG. 1). Further openings 19, positioned between the sample wells 16, open the hollows to the top surface 15 of the block. A central platform 20 occupies the space that would otherwise be occupied by a mass reduction hole similar to the openings 19. When the block 11 is used as a support block for a disposable plastic well plate (not shown) that has plastic wells corresponding to each well 16 in the block, the platform 20 will prevent the wells of the disposable plastic plate from being incorrectly placed in the mass reduction holes 19 rather than in the wells 16. This feature is explained in more detail below in connection with FIGS. 6 and 7.

Among the variations of the hollows shown in FIG. 1 are a series of unconnected parallel hollows, and hollows lacking the openings 19 to the top surface 15 of the block. The inclusion or omission of intersecting hollows and openings to the top surface will depend on the desired balance between stiffness and reduced mass, which may vary with the materials of construction, the dimensions of the block, and the manner in which the block is to be used.

Figure 2:
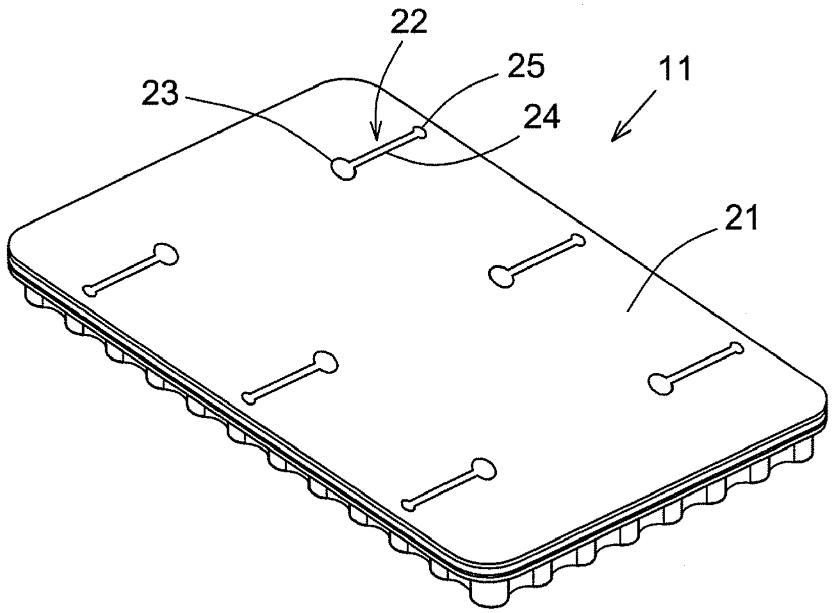
FIG. 2 is a perspective view of the sample block of FIG. 1 inverted to show the bottom surface of the block.

The underside of the sample block 11 of FIG. 1 is shown in FIG. 2. The bottom surface 21 of the block is a flat planar surface parallel to the top surface 15 of FIG. 1, and the thermoelectric modules or other heating or cooling components, although not shown, are pressed against this bottom surface 21. The bottom surface contains a series of depressions 22 to accommodate temperature sensors and electrical connections to the sensors. Thermistors or other types of sensors that can function effectively in sample blocks of this construction will be readily apparent to those skilled in temperature measurement or in the use of laboratory equipment in general. Each depression 22 includes an inner well 23 for the sensor itself, positioned toward the center of the surface, a slot 24 to accommodate electric leads to the sensor, and an outer well 25 near the periphery of the block for electrical connections to external circuitry.

Figure 3:
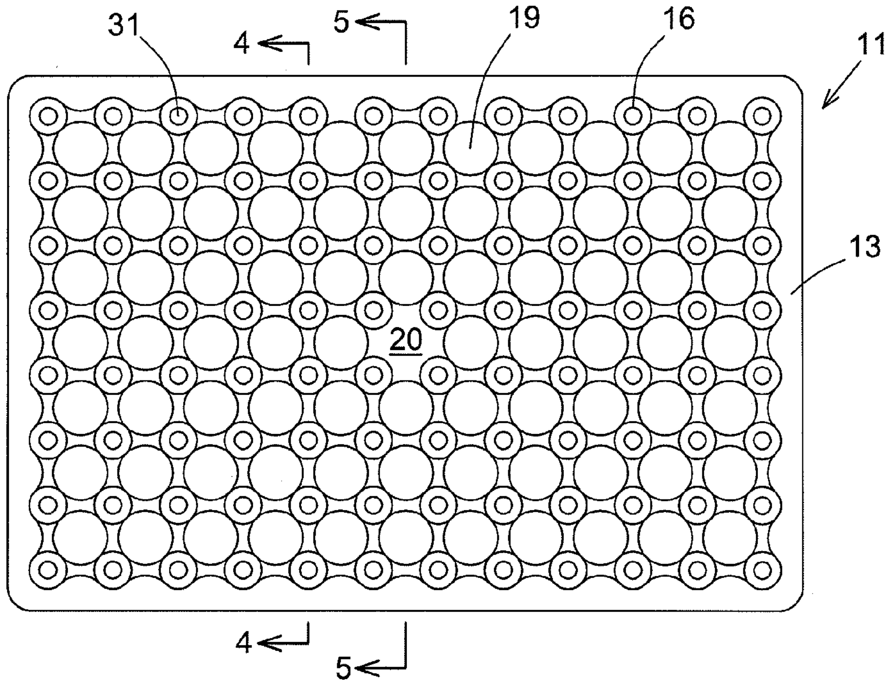
FIG. 3 is a plan view of the sample block of FIG. 1.

A plan view of the sample block 11 from above is provided in FIG. 3. The flange 13, sample wells 16, and upper openings 19 for the hollows are all visible in this view. The openings 19 leading to the hollows are larger in diameter than the mouths of the wells 16 for maximum mass reduction and yet provide sufficient connecting walls between the wells to retain the integrity and rigidity of the wells. Each well 16 tapers to a floor 31 that is of smaller diameter than the opening of the well and that can be tapered. The openings 19 leading to the hollows are not tapered, and the floor below each opening is either flat or tapered, depending on how the opening is formed.

Figure 4:
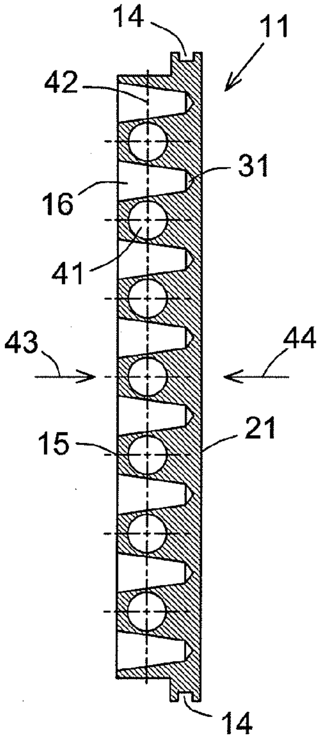
FIG. 4 is a cross section of the sample block of the preceding Figures taken along the line 4-4 of FIG. 3.

FIG. 4 is a cross section of the sample block 11 of the preceding Figures along the line 4-4 of FIG. 3. The cross section passes through the centers of the sample wells 16 and shows that the floors 31 of the wells are themselves tapered. The tapering of the wells, and particularly of the floors of the wells, facilitates the removal of fluids from the wells at stages of the reaction process where such removal is needed. The cross section also shows a first set of passages 41 that form part of the hollows that reduce the mass of the block. These passages 41 are parallel to the upper surface 15 and the lower surface 21 of the block 11 and extend the full length of the block, passing between the rows of wells 16. The centers of the passages 41 are as close as possible to the neutral plane 42 of the block. The term “neutral plane” is used herein to denote the plane of the block that experiences the least stress when the block is placed under a bending force from either above or below. Specifically, when a force is applied to the center of block from above in the direction of the arrow 43 while the edges of the block are held stationary to resist the force, the portion of the block above the neutral plane 42 will be compressed horizontally inward and the portion below the neutral plane will be stressed horizontally outward. Likewise, when a force is applied to the block from below in the direction of the arrow 44 while the edges of the block are again held stationary to resist the force, the portion of the block below the neutral plane 42 will be compressed horizontally inward and the portion above the neutral plane will be stressed horizontally outward. In both cases, the neutral plane 42 itself will be under little or no horizontal stress, either inward (compressive) or outward (expansive). The neutral plane will generally be at or near the midpoint of the thickness of the block, but its location may vary with the mass distribution through the block. The location of the neutral plane is readily determined by standard stress analyses.

Figure 5:
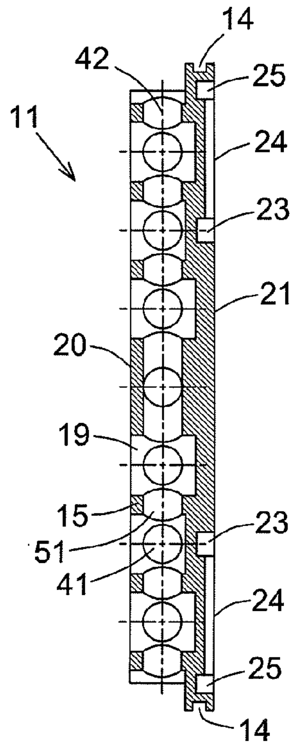
FIG. 5 is a cross section of the sample block of the preceding Figures taken along the line 5-5 of FIG. 3.

The cross section of FIG. 5 is taken along the line 5-5 of FIG. 3. The wells are not visible in this cross section. The cross section shows the passages 41 that are shown in FIG. 4, as well as a second set of passages 51 that run perpendicular to the first set of passages 41 and that also form part of the hollows that reduce the mass of the block. The passages 51 of the second set pass between adjacent columns of wells rather than rows and extend the width of the block 11 rather than the length, intersecting the passages 41 of the first set. At each intersection of the passages is the opening 19 to the top surface 15 and a recess 52 opposite the opening. Like the first set of passages 41, the passages 51 of the second set are parallel to both the top surface 15 and the bottom surface 21 of the block 11 and pass between the wells, and are at the same level in the block, relative to the top surface 15 and the bottom surface 21, as the first set. The centers of both sets of passages thus lie in, or close to, the neutral plane 42. Also visible in this view are the indentations in the bottom surface 21 for the temperature sensor, in each case including the sensor well 23, the peripheral well 25 for electrical connections to external circuitry, and the slot 24 joining the sensor well to the peripheral well.

While the passages 41 in FIGS. 4 and 5 and likewise the passages 51 in FIG. 5 are circular in cross section, passages of non-circular cross sections will serve equally as well, and in some cases may offer an advantage by fitting better in between the wells. Thus, trapezoidal, triangular, square, or rectangular cross sections can be used. Also, while each set of passages 41, 51 is arranged in a single layer, multiple layers of horizontal passages can be used as well. As in the case of passages with non-circular cross sections, layered or stacked passages may, depending on the geometry of the block and its wells, offer advantages by fitting better between rows or columns of wells, particularly wells that are tapered.

Figure 6:
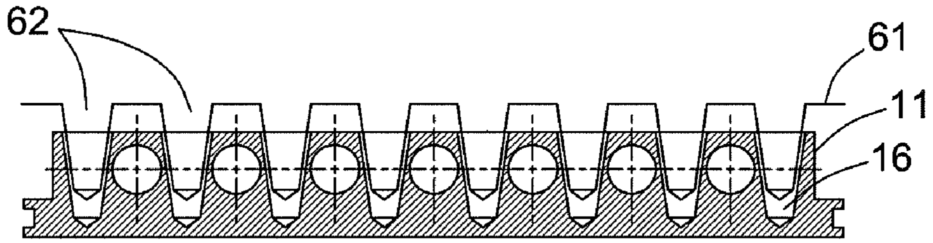
FIG. 6 is another view of the cross section of FIG. 3.
Figure 7:
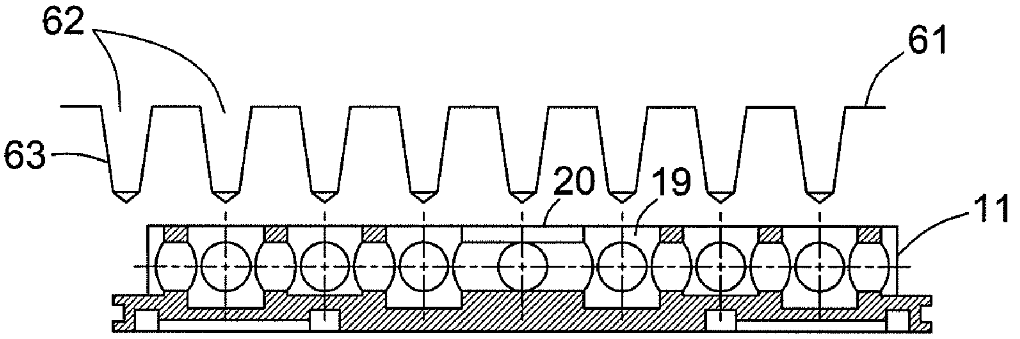
FIG. 7 is another view of the cross section FIG. 4.

FIGS. 6 and 7 are further views of the same cross sections shown in FIGS. 4 and 5, respectively, together with a disposable sample plate 61. The plate is formed of a thin sheet of plastic or other disposable material and is contoured to form sample wells 62. The wells have undersurfaces 63 (visible most clearly in FIG. 7) to which the wells 16 of the sample block 11 are complementary in contour. The wells in the block thus provide intimate surface contact with the wells in the sample plate for rapid heat transfer to the reaction mixtures in the sample plate. Proper alignment of the wells 62 in the plate with the wells 11 in the block is shown in FIG. 6. Since the mass reduction openings 19 in the block 11 are large enough to receive the wells 62 of the sample plate, the user might inadvertently misalign the plate and block by attempting to place the wells 62 of the plate in the mass reduction openings 19 rather than in the proper wells 16. Such misalignment would defeat the heat transfer functions of the block. The platform 20 prevents this misalignment by abutting the undersurface of the central sample well. In general, this prevention is achieved by using mass reduction openings that are fewer in number than the number of wells 62 in the sample plate, and likewise less than the number of temperature control wells 16 in the block. Thus, at least one platform is present on the block surface where an indentation would otherwise lie, the platform disrupting the continuous indentation pattern. Preferably, the platform is in the center of the indentation array.

Figure 8:
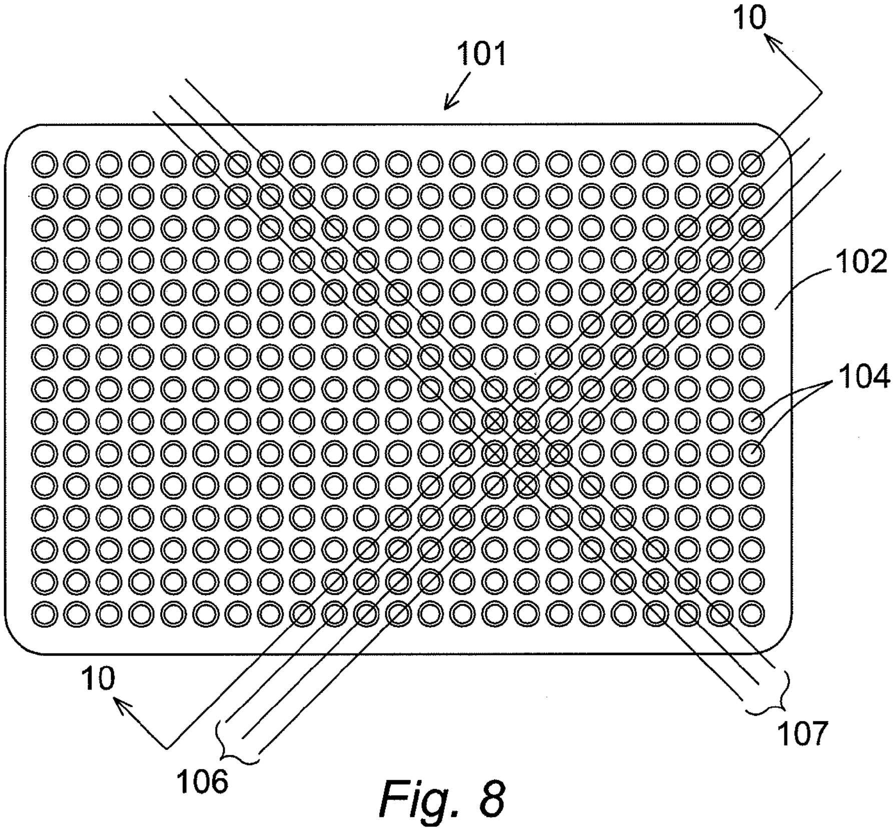
FIG. 8 is a top view of a second sample block in accordance with the present invention.
Figure 9:
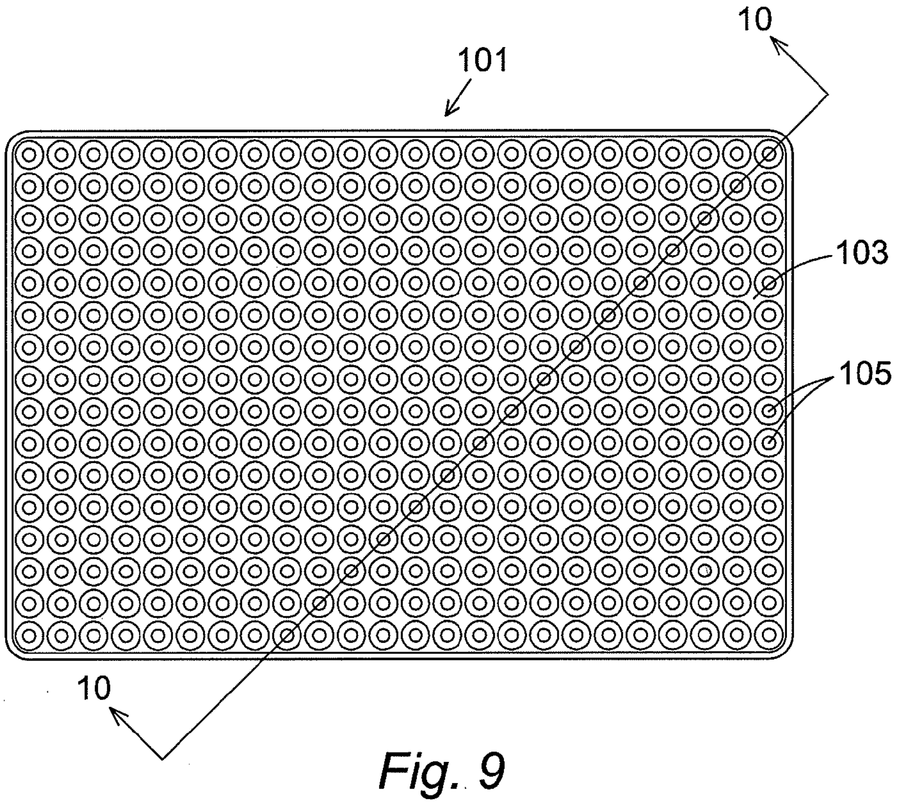
FIG. 9 is a bottom view of the sample block of FIG. 8.
Figure 10:
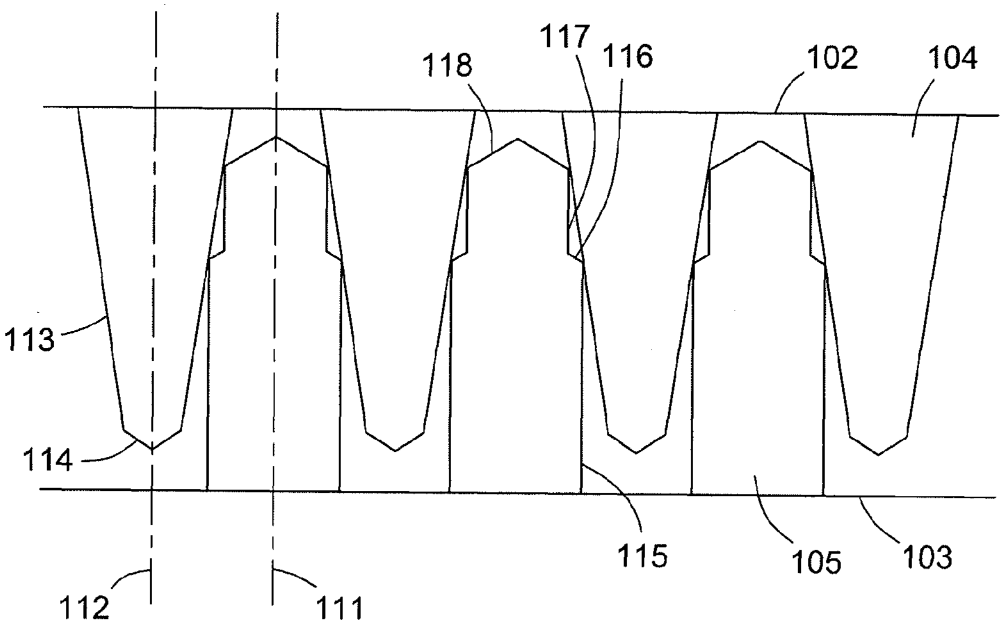
FIG. 10 is a cross section of the block of FIGS. 8 and 9 taken along the line 10-10 of FIGS. 8 and 9.

FIGS. 8, 9, and 10 are views of another sample block 101 in accordance with the present invention. The top surface 102 of the block 101 is shown in FIG. 8, the bottom surface 103 in FIG. 9, and a diagonal cross section in FIG. 10. The sample wells 104 are visible in FIG. 8 since they are open to the top surface 102. The sample wells form a 15×23 rectangular array, with a center-to-center spacing of 4.5 mm (0.18 inch). The mass reduction wells 105 are visible in FIG. 9 since they are open to the bottom. The mass reduction wells 105 are positioned between the sample wells 104 at the intersections of diagonal lines 106, 107 (shown in FIG. 8) connecting the centers of the sample wells 104. This achieves the maximum density of both the sample wells 104 and the mass reduction wells 105.

The cross section of FIG. 10 is take along the line 10-10 of FIGS. 8 and 9 to show the relative positions of the sample wells 104 and the mass reduction wells 105 and their profiles. Each well in both sets of wells is a cavity of revolution about a central axis 111, 112. Each sample well 104 is tapered by having both a frustoconical section 113 adjacent to the mouth of the well at the top surface 102 of the sample block and a conical section 114 at the base of the well. Each mass reduction well 105 is also tapered but in the opposite direction since the mass reduction wells are inverted. The taper in the mass reduction wells is formed by a straight cylindrical section 115 at the mouth of each well at the bottom surface 103 of the sample block, joined successively to a frustoconical section 116, a second straight cylindrical section 117 of narrower diameter than the first, and a short conical section 118 at the ceiling of the inverted well. The opposing tapers of the sample wells and the mass reduction wells allow for the maximum utilization of the volume of the sample block.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

It is emphasized that the structures shown in the Figures and described in detail above are mere examples of the invention whose scope is defined by the claims appended hereto. Further variations in the shapes, arrangements, dimensions, and materials used in the implementation of this invention that incorporate the basic elements of the invention as express in the claims will be readily apparent to those skilled in the art of laboratory equipment design, construction, and use.

What is claimed is:

1. A combination sample plate and support block for use in performing a plurality of chemical reactions simultaneously at controlled temperatures, said combination comprising:

a sample plate shaped to form an array of sample wells having undersides with selected contours defined by a floor and side walls of each well; and a support block of unitary construction having an upper surface and comprising a single array of support wells open to said upper surface, equal in number to said sample wells, and complementary in contour to said undersides of said sample wells such that when said sample plate rests on said support block with said sample wells inside said support wells, said undersides of said sample wells are in intimate surface contact with said support wells extending along said floor and side walls of each well, said surface further comprising a single array of indentations in said upper surface positioned between said support wells, said array of indentations being complementary with said array of sample wells except for a single platform at the center of said array of indentations, said platform positioned to prevent placement of said sample wells in said indentations while allowing placement of said sample wells in said support wells.

2. The combination of claim 1 wherein said array of sample blocks and said array of support wells are rectangular arrays.

* * * * *